(12) United States Patent
Liang et al.

(10) Patent No.: US 8,877,248 B1
(45) Date of Patent: *Nov. 4, 2014

(54) SUSTAINED-RELEASE FORMULATIONS OF TOPIRAMATE

(71) Applicant: Supernus Pharmaceuticals, Inc., Rockville, MD (US)

(72) Inventors: Likan Liang, Boyds, MD (US); Hua Wang, Clarksville, MD (US); Padmanabh P. Bhatt, Rockville, MD (US); Michael L. Vieira, Gaithersburg, MD (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/330,423

(22) Filed: Jul. 14, 2014

Related U.S. Application Data

(63) Continuation of application No. 12/926,936, filed on Dec. 17, 2010, which is a continuation of application No. 11/941,475, filed on Nov. 16, 2007, now Pat. No. 8,298,576.

(60) Provisional application No. 60/859,502, filed on Nov. 17, 2006.

(51) Int. Cl.
*A61K 9/16* (2006.01)
*A61K 9/50* (2006.01)
*A61K 31/7048* (2006.01)

(52) U.S. Cl.
CPC ............ *A61K 9/5042* (2013.01); *A61K 31/7048* (2013.01)
USPC ............................ 424/490; 514/25; 427/2.21

(58) Field of Classification Search
None
See application file for complete search history.

(56) References Cited

U.S. PATENT DOCUMENTS

| | | |
|---|---|---|
| 2,528,378 A | 10/1950 | Manheimer et al. |
| 2,675,619 A | 4/1954 | Cone |
| 2,677,700 A | 5/1954 | Jackson et al. |
| 2,781,354 A | 2/1957 | Mannheimer et al. |
| 2,979,578 A | 4/1961 | Curtis |
| 2,996,431 A | 8/1961 | Barry |
| 3,036,118 A | 5/1962 | Jackson et al. |
| 3,139,383 A | 6/1964 | Neville et al. |
| 3,535,307 A | 10/1970 | Moss et al. |
| 3,811,444 A | 5/1974 | Heller et al. |
| 3,829,506 A | 8/1974 | Schmolka et al. |
| 3,962,414 A | 6/1976 | Michaels |
| 3,992,518 A | 11/1976 | Chien et al. |
| 4,066,747 A | 1/1978 | Capozza |
| 4,070,347 A | 1/1978 | Schmitt |
| 4,079,038 A | 3/1978 | Choi et al. |
| 4,083,949 A | 4/1978 | Benedikt |
| 4,093,709 A | 6/1978 | Choi et al. |
| 4,290,426 A | 9/1981 | Luschen et al. |
| 4,434,153 A | 2/1984 | Urquhart et al. |
| 4,513,006 A | 4/1985 | Maryanoff et al. |
| 4,721,613 A | 1/1988 | Urquhart et al. |
| 4,727,064 A | 2/1988 | Pitha |
| 4,752,470 A | 6/1988 | Mehta |
| 4,757,128 A | 7/1988 | Domb et al. |
| 4,853,229 A | 8/1989 | Theeuwes |
| 4,938,763 A | 7/1990 | Dunn et al. |
| 4,997,904 A | 3/1991 | Domb |
| 5,030,447 A | 7/1991 | Joshi et al. |
| 5,175,235 A | 12/1992 | Domb et al. |
| 5,180,589 A | 1/1993 | Joshi et al. |
| 5,225,202 A | 7/1993 | Hodges et al. |
| 5,256,440 A | 10/1993 | Appel et al. |
| 5,378,475 A | 1/1995 | Smith et al. |
| 5,478,577 A | 12/1995 | Sackler et al. |
| 5,500,227 A | 3/1996 | Oshlack et al. |
| 5,576,311 A | 11/1996 | Guy |
| 5,753,693 A | 5/1998 | Shank |
| 5,760,007 A | 6/1998 | Shank et al. |
| 5,773,019 A | 6/1998 | Ashton et al. |
| 5,935,933 A | 8/1999 | Shank et al. |
| 5,955,096 A | 9/1999 | Santos et al. |
| 5,985,312 A | 11/1999 | Jacob et al. |
| 5,998,380 A | 12/1999 | Ehrenberg et al. |
| 6,123,965 A | 9/2000 | Jacob et al. |
| 6,156,348 A | 12/2000 | Santos et al. |
| 6,159,501 A | 12/2000 | Skinhoj |
| 6,191,117 B1 | 2/2001 | Kozachuk |

(Continued)

FOREIGN PATENT DOCUMENTS

| | | |
|---|---|---|
| CN | 1130352 A | 9/1996 |
| WO | WO 93/21906 A1 | 11/1993 |

(Continued)

OTHER PUBLICATIONS

US 6,103,281, 08/2000, DelDuca et al. (withdrawn).

(Continued)

*Primary Examiner* — Suzanne Ziska
(74) *Attorney, Agent, or Firm* — Foley & Lardner LLP; Sunit Talapatra

(57) ABSTRACT

Pharmaceutical compositions of topiramate for once-a-day oral administration are provided. The formulations comprise a sustained-release component and an optional immediate-release component, the compositions of which can be selectively adjusted, respectively, to release the active ingredient along a pre-determined release profile. Method of treating or preventing pathological disorders in mammalian subjects comprising the administration of the novel formulations disclosed herein is also provided.

20 Claims, 6 Drawing Sheets

(56) References Cited

U.S. PATENT DOCUMENTS

| | | | |
|---|---|---|---|
| 6,197,346 B1 | 3/2001 | Mathiowitz et al. | |
| 6,201,010 B1 | 3/2001 | Cottrell | |
| 6,217,908 B1 | 4/2001 | Mathiowitz et al. | |
| 6,235,311 B1 | 5/2001 | Ullah et al. | |
| 6,248,363 B1 | 6/2001 | Patel et al. | |
| 6,294,192 B1 | 9/2001 | Patel et al. | |
| 6,319,903 B1 | 11/2001 | Carrazana et al. | |
| 6,344,215 B1 | 2/2002 | Bettman et al. | |
| 6,365,187 B2 | 4/2002 | Mathiowitz et al. | |
| 6,368,586 B1 | 4/2002 | Jacob et al. | |
| 6,479,467 B1 | 11/2002 | Buchanan et al. | |
| 6,503,884 B1 | 1/2003 | Ehrenberg et al. | |
| 6,514,531 B1 | 2/2003 | Alaux et al. | |
| 6,524,620 B2 | 2/2003 | Chen et al. | |
| 6,559,293 B1 | 5/2003 | Almarsson et al. | |
| 6,562,865 B1 | 5/2003 | Codd et al. | |
| 6,569,463 B2 | 5/2003 | Patel et al. | |
| 6,696,091 B2 | 2/2004 | Thakur et al. | |
| 6,699,840 B2 | 3/2004 | Almarsson et al. | |
| 6,797,283 B1 | 9/2004 | Edgren et al. | |
| 6,923,988 B2 | 8/2005 | Patel et al. | |
| 7,018,609 B2 | 3/2006 | Hwang Pun et al. | |
| 7,195,778 B2 | 3/2007 | Fleshner-Barak et al. | |
| 7,611,722 B2 | 11/2009 | Lerner et al. | |
| 7,737,133 B2 | 6/2010 | Devane et al. | |
| 7,763,635 B2 | 7/2010 | Kidane et al. | |
| 2002/0044962 A1 | 4/2002 | Cherukuri et al. | |
| 2002/0054907 A1 | 5/2002 | Devane et al. | |
| 2002/0064563 A1 | 5/2002 | Thakur et al. | |
| 2002/0150616 A1 | 10/2002 | Vandecruys | |
| 2003/0017972 A1 | 1/2003 | Pun et al. | |
| 2003/0064097 A1 | 4/2003 | Patel et al. | |
| 2003/0072802 A1 | 4/2003 | Cutler | |
| 2003/0091630 A1 | 5/2003 | Louie-Helm et al. | |
| 2003/0133985 A1 | 7/2003 | Louie-Helm et al. | |
| 2003/0147952 A1 | 8/2003 | Lim et al. | |
| 2003/0157173 A1 | 8/2003 | Percel et al. | |
| 2003/0166581 A1 | 9/2003 | Almarsson et al. | |
| 2003/0215496 A1 | 11/2003 | Patel et al. | |
| 2003/0225002 A1 | 12/2003 | Livingstone | |
| 2004/0002462 A1 | 1/2004 | Najarian | |
| 2004/0022844 A1 | 2/2004 | Hasenzahl et al. | |
| 2004/0028729 A1 | 2/2004 | Shojaei et al. | |
| 2004/0028735 A1 | 2/2004 | Kositprapa | |
| 2004/0052843 A1 | 3/2004 | Lerner et al. | |
| 2004/0053853 A1 | 3/2004 | Almarsson et al. | |
| 2004/0082519 A1 | 4/2004 | Hedner et al. | |
| 2004/0091529 A1 | 5/2004 | Edgren et al. | |
| 2004/0096501 A1 | 5/2004 | Vaya et al. | |
| 2004/0109894 A1 | 6/2004 | Shefer et al. | |
| 2004/0115262 A1 | 6/2004 | Jao et al. | |
| 2004/0122104 A1 | 6/2004 | Hirsh et al. | |
| 2004/0132826 A1 | 7/2004 | Hirsh et al. | |
| 2004/0156901 A1 | 8/2004 | Thakur et al. | |
| 2004/0157785 A1 | 8/2004 | Connor | |
| 2004/0185097 A1 | 9/2004 | Kannan et al. | |
| 2004/0234601 A1 | 11/2004 | Legrand et al. | |
| 2004/0258758 A1 | 12/2004 | Gustow et al. | |
| 2005/0053653 A1 | 3/2005 | Kidane et al. | |
| 2005/0058707 A1 | 3/2005 | Reyes et al. | |
| 2005/0069587 A1 | 3/2005 | Modi et al. | |
| 2005/0106242 A1 | 5/2005 | Yan et al. | |
| 2005/0106247 A1 | 5/2005 | Venkatesh et al. | |
| 2005/0129765 A1 | 6/2005 | Li et al. | |
| 2005/0136108 A1 | 6/2005 | Yam et al. | |
| 2005/0169982 A1 | 8/2005 | Almarssoo et al. | |
| 2005/0169992 A1 | 8/2005 | Jao et al. | |
| 2005/0175697 A1 | 8/2005 | Edgren et al. | |
| 2005/0191343 A1 | 9/2005 | Liang | |
| 2005/0220596 A1 | 10/2005 | Gaedy et al. | |
| 2006/0018933 A1 | 1/2006 | Vaya et al. | |
| 2006/0018934 A1 | 1/2006 | Vaya et al. | |
| 2006/0024365 A1 | 2/2006 | Vaya et al. | |
| 2006/0034927 A1 | 2/2006 | Casadevall et al. | |
| 2006/0078609 A1 | 4/2006 | Vandecruys et al. | |
| 2006/0105045 A1 | 5/2006 | Buchanan et al. | |
| 2006/0121112 A1* | 6/2006 | Jenkins et al. | 424/468 |
| 2006/0147527 A1 | 7/2006 | Bachmann et al. | |
| 2006/0223762 A1 | 10/2006 | Ehrenberg et al. | |
| 2006/0233892 A1 | 10/2006 | Hendrix | |
| 2007/0212411 A1 | 9/2007 | Fawzy et al. | |
| 2008/0085306 A1* | 4/2008 | Nangia et al. | 424/458 |
| 2008/0131501 A1 | 6/2008 | Liang et al. | |
| 2011/0287099 A1 | 11/2011 | Liang et al. | |

FOREIGN PATENT DOCUMENTS

| | | |
|---|---|---|
| WO | WO 01/37808 A1 | 5/2001 |
| WO | WO 02/03984 A2 | 1/2002 |
| WO | WO 02/43731 A3 | 6/2002 |
| WO | WO 2004/022037 A1 | 3/2004 |
| WO | WO 2004/078162 A1 | 9/2004 |
| WO | WO 2004/078163 A2 | 9/2004 |
| WO | WO 2005/030166 A1 | 4/2005 |
| WO | WO 2005/079748 A2 | 9/2005 |
| WO | WO 2006/009403 A1 | 1/2006 |
| WO | WO 2006/119153 A2 | 11/2006 |
| WO | WO 2007/002318 | 1/2007 |

OTHER PUBLICATIONS

Adin et al., "Topiramate Serum Concentration-to-Dose Ratio," Therapeutic Drug Monitoring, Jun. 2004; 26(3):251-257.

Bahk et al., "Topiramate and divalproex in combination with risperidone for acute mania: a randomized open-label study," Progress in Neuropsychopharmacology & Biological Psychiatry, 2005, 29(1):115-121.

Beaumanoir, Anne, "The Landau-Kleffner syndrome", In: Roger et al., Eds. *Epileptic Syndromes in Infancy, Childhood, and Adolescence*, 2nd Ed., London, England: John Libby, pp. 231-244, 1992.

Berge et al., "Pharmaceutical Salts", J. Pharm, Sci., Jan. 1977, 66(1): 1-19.

Berlant, Jeffery L., M.D., Ph.D., "Topiramate in Posttraumatic Stress Disorder: Preliminary Clinical Observations," J. Clin. Psychiatry, 2001, 62(Suppl 17):60-63.

Brandes et al., "Topiramate for Migraine Prevention," JAMA, Feb. 25, 2004, 291(8):965-973.

Carpenter et al., "Do obese depressed patients respond to topiramate? A retrospective chart review," J. Affect. Disord., 2002, 69(1-3):251-255.

Chen et al., "Combination Treatement of Clozapine and Topiramate in Resistant Rapid-Cycling Bipolar Disorder," Clin. Neuropharmacol., May-Jun. 2005, 28(3):136-138.

Coleman et al., "Polymer reviewed: A practical guide to polymer miscibility," Jul. 1990, 31:1187-1230.

Contin et al., "Topiramate Therapeutic Monitoring in Patients with Epilepsy: Effect of Concomitant Antiepileptic Drugs," Ther. Drug Monit., 2002, 24(3):332-337.

D'Amico et al., "Topiramate in migraine prophylaxis," Neurological Sciences, 2005, 26(Suppl 2):S130-S133.

Deckers et al., "Selection of Antiepileptic Drug Polytherapy Based on Mechanisms of Action: The Evidence Reviewed," Epilepsia, 2000, 41(11):1364-1374.

Diener et al., "Topiramate in migrain prophylaxis: Results from a placebo-controlled trail with propranolol as an active control," J. Neurol., 2004, 251(8):943-950.

Dorado et al., "Topiramato en enfermedades comorbidas: epilepsia y migrana," Rev. Neurol., 2006, 43(4):193-196.

Duchene et al., "Pharmaceutical and Medical Aspects of Bioadhesive Systems for Drug Administration," Drug Dev. Ind. Pharm., 1988, 14(2&3):283-318.

Erfurth et al., "Bupropion as Add-On Strategy in Difficult-to-Treat Bipolar Depressive Patients," Neuropsychobiology, 2002, 45(Suppl 1):33-36.

Felmeister, Alvin Ph.D., "Powders," Remington's Pharm. Sci., 14th Ed., 1970, Chapter 86, 1626-1628.

Ferrari et al., "Influence of Dosage, Age, and Co-Medication on Plasma Topiramate Concentrations in Children and Adults with

(56) References Cited

OTHER PUBLICATIONS

Severe Epilepsy and Preliminary Observations on Corrections with Clinical Response," Therapeutic Drug Monitoring, 2003, 25(6):700-708.
Ferrari et al., "Rizatriptan: a new milestone in migraine treatment," Cephalalgia, 2000, 20(Suppl 1):1.
Fincher, Julian H., "Particle Size of Drugs and Its Relationship to Absorption and Activity," J. Pharm. Sci., Nov. 1968, 57(11):1825-1835.
Fisher et al., "Synergism between Topiramate and Budipine in Refractory Status in Epilepticus in the Rat," Epilepsia, 2004, 45(11):1300-1307.
François et al., "The combination of topiramate and diazepam is partially neuroprotective in the hippocampus but not antiepileptogenic in the lithium-pilocarpine model of temporal lobe epilepsy," Epilepsy Research, 2006, 72:147-163.
Gurny et al., "Bioadhesive intraoral release systems: design, testing and analysis," Biomaterials, Nov. 1984, 5:336-340.
Hershey et al., "Effectiveness of Topiramate in the Prevention of Childhood Headaches," Sep. 2002;42(8):810-818.
Hoes et al., "The Application of Drug-Polymer Conjugates in Chemotherapy," Drug Carrier Systems, 1989, 9:57-109.
Hollander et al., "Topiramate plus paroxetine in treatment-resistant obsessive-complusive disorder," Int. Clin. Psychopharmacol., 2006, 21(3): 189-191.
International Search Report and Written Opinion mailed Sep. 2, 2008, in PCT/US2007/19208. 10 pages.
Ioannides-Demos et al., "Pharmacotherapy for Obesity," Drugs, 2005, 65(10):1391-1418.
Johnson et al., "Oral topiramate for treatmetn of alcohol dependence: a randomised controlled trial," The Lancet, May 17, 2003, 361(9370):1677-1685.
Kellett et al., "Topiramate in clinical practice: first year's postlicensing experience in a specialist epilepsy clinic," J. Neurol. Neurosurg. and Psych., 1999;66:759-763.
Lainez et al., "Topiramate in the Prophylactic Treatment of Cluster Headache," Headache, Jul./Aug. 2003, 43(7):784-789.
Lalonde et al., "Additive effects of leptin and topiramate in reducing fate deposition in lean and obese ob/ob mice," Physiology & Behavior, 2004, 80(4):415-420.
Lee et al., "The Effects of Adjunctive Topiramate on Cognitive Function in Patients with Epilepsy," Epilepsia, 2003; 44(3):339-347.
Lehr et al., "Intestinal Transit of Bioadhesive Microspheres in an in situ Loop in the Rat—A Comparative Study with Copolymers and Blends Based on Poly(acrylic acid)," Journal of Controlled Release, 1990, 13:51-62.
Leong et al., "Polymeric controlled drug delivery," Adv. Drug Delivery Rev., 1987, 1:199-233.
Linhardt, Robert J. "Biodegradable Polymers for Controlled Release of Drugs," Controlled Release of Drugs, 1989, Chapter 2, 53-95.
Liu et al., "Preparation, characterization and in vivo evaluation of formulation of baicalein with hydroxypropyl-beta-cyclodextrin," International Journal of Pharmaceuticals, 2006, 312:137-147.
Longer, Mark A., Ph.D., "Sustained-Release Drug Delivery Systems," Remington's Pharmaceutical Sciences, 18th Edition, 1990, Chapter 91, 1676-1693.
Lu et al., "Dimensionless presentation for drug release from a coated pure drug bead: 1. Analysis, "Inter. J. of Pharm., 1994, 112:105-116.
Lu et al., "Dimensionless presentation for drug release from a coated pure drug bead: 2. Experiment," Inter. J. of Pharm., 1994, 112:117-124.
Luszczki et al., "Interactions of Lamotrigine with Topiramate and First-Generation Antiepileptic Drugs in the Maximal Electroshock Test in Mice: An Isobolographic Analysis," Epilepsia, 2003, 44(8):1003-1013.
Mathew et al., "Prophylaxis of Migraine, Transformed Migraine, and Cluster Headache with Topiramate," Headache, Sep. 2002, 42(8):796-803.

McElroy et al., "Topiramate in the Treatment of Binge Earing Disorder Associated with Obesity: A Randomized, Placebo-Controlled Trial," Am. J. Psychiatry, Feb. 2003, 160(2):255-261.
Meador et al., "Cognitive and behavioral effects of lamotrigine and topiramate in healthy volunteers," Neurology, Jun. 2005, 64:2108-2114.
Mikos et al., "Interaction of Polymer Microspheres with Mucin Gels as a Means of Characterizing Polymer Retention on Mucus," Journal of Colloid and Interface Science, May 1991, 143(2): 366-373.
Morton et al., "Diagnosis and treatment of epilepsy in children and adolescents", Drugs, Mar. 1996, 51(3):399-414.
Mosek et. al., "Topiramate in the treatment of refractory chronic daily headache. An open trial," Journal of Headache and Pain, 2005, 6:77-80.
O'Connor et al., "Powders," Remington's Pharmaceutical Sciences, 18th Edition, 1990, Chapter 88, 1615-1632.
Park et al., "Alternative Approaches to Oral Controlled Drug Delivery: Bioadhesives and In-Situ Systems," Recent Advances in Drug Delivery, Plenum Press, New York, 1984, 163-183.
Pascual et al., "Testing the combination beta-blocker plus topiramate in refractory migraine," Acta Neurol. Scand., 2007, 115(2):81-83.
Physician's Desk Reference, $60^{th}$ Edition, 2006, pp. 2438-2447, entry for TOPAMAX®.
Physicians' Desk Reference 59th edition, 2541-2548 (2005).
Physician's Desk Reference, 56th ed., 2590-2595 (2002).
Pies, Ronald M.D., "Combining Lithium and Anticonvulsants in Bipolar Disorder: A Review," Annals of Clinical Psychiatry, Dec. 2002, 14(4):223-232.
Porter, Stuart C., Ph.D., "Coating of Pharmaceutical Dosage Forms," Remington's Pharmaceutical Sciences, 18th Edition, Chapter 90, 1666-1675.
Potter et al., "A Double-Blind, Randomized, Placebo-Controlled, Parallel Study to Determine the Efficacy of Topiramate in the Prophylactic Treatment of Migraine," Neurology, Apr. 2000, 54(Suppl 3):A15.
Rudnic et al., "Oral Solid Dosage Forms," Remington's Pharmaceutical Sciences, 18th Edition, 1990, Chapter 89, 1633-1665.
Silberstein et al., "Topiramate in Migraine Prevention," Arch. Neurol., Apr. 2004, 61(4):490-495.
Siniscalchi et al., "Combined topiramate and declorazepam therapy in a patient affected by essential tremor," Parkinsonism Relat. Disord., 2007, 13(2):129-130.
Smart et al., "An in-vitro investigation of mucosa-adhesive materials for use in controlled drug delivery," J. Pharm. Pharmacol., 1984, 36:295-299.
Sofuoglu et al., "Effects of topiramate in combination with intravenous nicotine in overnight abstinent smokers," Psychopharmacology, 2006, 184(3-4): 645-651.
Storey et al., "Topiramate in Migraine Prevention: A Double-Blind Placebo-Controlled Study," Headache, Nov./Dec. 2001, 41(10):968-975.
Thompson et al., "Effects of topiramate on cognitive function," J. Neurol. Neurosurg and Psych., 2000; 69:634-641.
Toplak et al., "Efficacy and safety of topiramate in combination with metformin in the teratment of obese subjects with type 2 diabetes: a randomized, double-blind placebo-controlled study," Int. J. Obes ., 2007, 31(1):138-146.
Von Seggern et al., "Efficacy of Topiramate in Migraine Prophylaxis: A Retrospective Chart Analysis," Neurology, Apr. 2000, 54(Suppl 3):A267-A268.
Weber, Marcus Vinicius Keche, M.D., "Topiramate for Obstructive Sleep Apnea and Snoring," Am. J. Psychiatry, May 2002, 159(5):872-873
Winkelman, John W., "Treatement of nocturnal eating syndrome and sleep-related eating disorder with topiramate," Sleep Medicine, 2003, 4(3):243-246.

* cited by examiner

*80% release time vs. %Wt. gain of Release-Controlling Coating*

*For Surelease® coated Extended Release Beads*

*80% release time vs. % Wt. gain of Release-Controlling Coating*

*For Surelease®/ Opadry® coated Extended Release Beads*

Mean (n= 16) PK Profiles from Bead Populations XR1, XR2 and XR3

Mean (n= 16) PK Profiles from the Immediate Release Formulations

Dissolution Profiles of Immediate Release Formulations

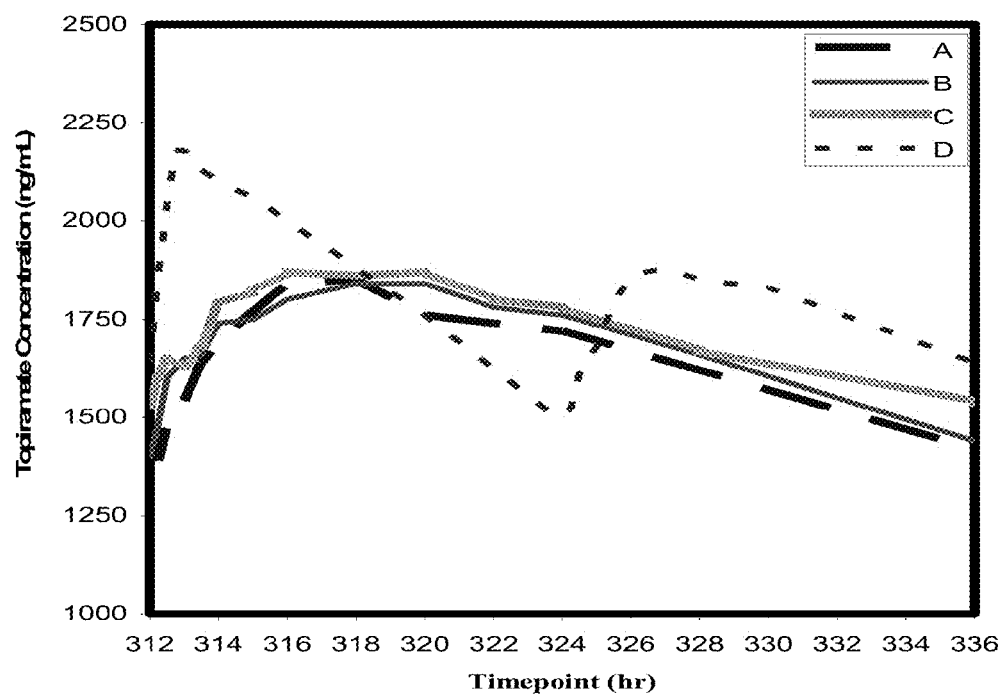
Fig.6. Mean PK Profiles for Sustained Release Formulations A, B, and C

SUSTAINED-RELEASE FORMULATIONS OF TOPIRAMATE

CROSS-REFERENCE TO RELATED APPLICATIONS

The present application is a Continuation of U.S. application Ser. No. 12/926,936, filed Dec. 17, 2010, which is a Continuation of U.S. application Ser. No. 11/941,475, filed Nov. 16, 2007, which claims benefit of U.S. Provisional Application No. 60/859,502, filed Nov. 17, 2006, the entire contents of which are incorporated herein by reference.

BACKGROUND OF THE INVENTION

Topiramate is a sulfamate substituted monosaccharide which under the trade name TOPAMAX® (Ortho-McNeil Pharmaceutical, Inc., Raritan, N.J., U.S.A.) has been approved for use as an antiepileptic agent, as an adjuvant therapy for patients with partial onset seizures or primary generalized tonic-clonic seizures, and for the prevention of migraine. See generally, Physician's Desk Reference, 60th ed., 2538-2447 (2006); see also, U.S. Pat. No. 4,513,006.

For the treatment of epilepsy, the recommended dose of Topamax® is 400 mg/day in one or multiple doses (Physician's Desk Reference, 60th ed., 2538-2447 (2006)). For adults with epilepsy, treatment is initiated with a dose of 25-50 mg/day, with the dose being titrated in increments of 25-50 mg at weekly intervals to the recommended or effective dose.

Topamax® is an immediate release formulation. Adverse effects associated with the administration of Topamax® include, but are not limited to, somnolence, dizziness, ataxia, speech disorders and related speech problems, psychomotor slowing, abnormal vision, difficulty with memory, paresthesia, diplopia, renal calculi (kidney stones), hepatic failure, pancreatitis, renal tubular acidosis, acute myopia and secondary angle closure glaucoma (Physician's Desk Reference, 60th ed., 2538-2447 (2006)).

Hence, though topiramate has a relatively long half-life of 21 hours in vivo, it has not been prescribed (or formulated) as a single, daily-dose, in part due to severe side-effects that often result with peak plasma levels of the drug when taken in high doses. Instead, Topamax® is typically taken in multiple, "divided" doses, usually twice-daily ("BID"). However, administration of the medicament in this manner is cumbersome and patients can forget to take their medication in a timely manner. What is more, each administration of a dose is associated with a peak in plasma concentrations of the drug, and the fluctuations associated with the peaks and valleys of blood plasma levels of the drug are undesirable. Therefore, there is a need for a formulation of topiramate, which reduces or eliminates the side effects associated with peaking and fluctuating plasma levels of the drug and preferably may be administered in a once-daily regimen.

New, highly soluble and bioavailable forms of topiramate are also needed in order to increase the safety and effectiveness of the drug.

The instant invention addresses these and other needs by providing a modified formulation of topiramate characterized by a sustained, non-pulsatile release of an active ingredient. This invention additionally provides an effective, once-daily dosage form of topiramate or salts thereof, which not only enables an effective single daily dose regimen to improve patient compliance but may also reduce some of the side effects of topiramate compared to the current or higher daily doses of immediate release topiramate formulations.

SUMMARY OF THE INVENTION

It is an object of the present invention to provide a sustained release formulation of topiramate for the treatment or prevention of a pathological condition in a mammalian subject, characterized by a sustained rate of topiramate release along a pre-determined release profile.

It is yet another object of the present invention to provide topiramate formulation wherein topiramate is released at a rate which results in a reduction in the frequency or severity of at least one side effect associated with the topiramate treatment.

It is a further object of the present invention to provide a sustained release formulation of topiramate that can be administered orally once a day.

It is an object of the present invention to provide a sustained release formulation of topiramate for oral administration to a mammalian subject comprising topiramate as an active ingredient, wherein the active ingredient is released from the formulation at a sustained rate along a pre-determined release profile, and wherein the sustained release formulation comprises an extended release (XR) component and an optional immediate release (IR) component.

In one embodiment of the invention, the extended release component is contained in at least one population of beads coated with a release controlling coating. The above-mentioned coating is specific for every bead population and determines its rate of release. Thus, every given bead population included into the formulation is characterized by its own specific rate of release.

In another embodiment of the invention, the sustained release topiramate formulation comprises an immediate release component in addition to an extended release component.

In a preferred embodiment of the invention, the immediate release component is an enhanced immediate release (EIR) composition.

The formulation of the present invention may be incorporated in any oral dosage form such as represented by, but not limited to, a tablet, a pill, a capsule, a troche, a sachet, and sprinkles.

It is yet another object of the present invention to provide a method of preparation of a sustained release formulation of topiramate, comprising an extended release component, and an optional immediate release component, wherein topiramate is released from the formulation at the sustained rate along the pre-determined release profile, the method comprising the steps of:

1. determining the desired release profile;
2. determining specific amounts of the extended release component and the immediate release component necessary to produce the pre-determined release profile; and
3. incorporating the specified amounts of the components into the formulation.

In one embodiment, the method of preparation additionally includes a process for providing an XR component contained in at least one population of beads, wherein every population of beads is characterized by its own rate of release. This process comprises the steps of 1. forming at least one population of topiramate-containing beads;
2. coating each population of beads with its own coating solution;

3. curing the coating for a period of time to produce a release controlling coating specific for each bead population, and 4. incorporating the beads into the formulation.

The method may optionally include a process for preparation of an IR component, which optionally is an enhanced immediate release (EIR) composition. The enhanced immediate release composition includes at least one agent selected from a group comprising complexing agents and enhancing agents. Without any limitations, the enhancing agents useful in the present invention may be selected from solubilizing agents, dissolution enhancing agents, absorption enhancing agents, penetration enhancing agents, surface active agents, stabilizing agents, enzyme inhibitors, p-glycoprotein inhibitors, multidrug resistance protein inhibitors or combinations thereof.

It is yet another object of the present invention to provide a method of treatment or prevention of a pathological condition in a mammalian subject by orally administering to the subject a therapeutically effective amount of a sustained release topiramate formulation of the instant invention. The pathological conditions that may be treated by the method of the present invention include neurological condition, psychiatric condition, diabetes and related disorders, cardiovascular condition, obesity, and any other condition or disorder that may be treated or prevented by topiramate administration.

DEFINITIONS

For the purposes of this invention, the term "topiramate" includes topiramate or any pharmaceutically acceptable salts thereof.

An "immediate release formulation" refers to a formulation that releases greater than or equal to about 80% of the pharmaceutical agent in less than or equal to about 1 hour.

For the purposes of this application, an enhancing agent ("enhancer") is defined as any non-pharmaceutically active ingredient that improves the therapeutic potential of a formulation.

The term "enhanced immediate release composition" as used herein describes an immediate release composition improved in terms of a therapeutic potential or treatment modality.

"Sustained release" is defined herein as release of a pharmaceutical agent in a continuous manner over a prolonged period of time.

By "prolonged period of time" it is meant a continuous period of time of greater than about 1 hour, preferably, greater than about 4 hours, more preferably, greater than about 8 hours, more preferably greater than about 12 hours, more preferably still, greater than about 16 hours up to more than about 24 hours.

As used herein, unless otherwise noted, "rate of release" or "release rate" of a drug refers to the quantity of drug released from a dosage form per unit time, e.g., milligrams of drug released per hour (mg/hr) or a percentage of a total drug dose released per hour. Drug release rates for dosage forms are typically measured as an in vitro rate of drug release, i.e., a quantity of drug released from the dosage form per unit time measured under appropriate conditions and in a suitable fluid. The time at which a specified percentage of the drug within a dosage form has been released from the dosage form is referred to as the "T.sub.x" value, where "x" is the percent of drug that has been released.

The release rates referred to herein are determined by placing a dosage form to be tested in a medium in an appropriate dissolution bath. Aliquots of the medium, collected at pre-set intervals, are then injected into a chromatographic system fitted with an appropriate detector to quantify the amounts of drug released during the testing intervals.

"C" denotes the concentration of drug in blood plasma, or serum, of a subject, and is generally expressed as mass per unit volume, for example nanograms per milliliter. For convenience, this concentration may be referred to herein as "drug plasma concentration", "plasma drug concentration" or "plasma concentration" which is intended to be inclusive of a drug concentration measured in any appropriate body fluid or tissue. The plasma drug concentration at any time following drug administration is referenced as Ctime, as in C9 hr or C4 hr, etc.

The maximum plasma drug concentration during the dosing period is referenced as Cmax, while Cmin refers to the minimum blood plasma drug concentration at the end of a dosing interval; and Cave refers to an average concentration during the dosing interval.

The "degree of fluctuation" is defined as a quotient (Cmax−Cmin)/Cave.

Persons of skill in the art will appreciate that blood plasma drug concentrations obtained in individual subjects will vary due to interpatient variability in the many parameters affecting drug absorption, distribution, metabolism and excretion. For this reason, unless otherwise indicated, when a drug plasma concentration is listed, the value listed is the calculated mean value based on values obtained from a groups of subjects tested.

The term "bioavailability" refers to an extent to which—and sometimes rate at which—the active moiety (drug or metabolite) enters systemic circulation, thereby gaining access to the site of action.

"AUC" is the area under the plasma concentration-time curve and is considered to be the most reliable measure of bioavailability. It is directly proportional to the total amount of unchanged drug that reaches the systemic circulation.

Side effect is defined herein as a secondary and usually adverse effect of a drug.

The term "beads", as used herein, includes, without any limitations on the nature and size thereof, any particles, spheres, beads, granules, pellets, particulates or any structural units that may be incorporated into an oral dosage form.

BRIEF DESCRIPTION OF THE DRAWINGS

FIG. 6 shows mean PK Profiles for Sustained Release Formulations A, B, and C.

DETAILED DESCRIPTION OF THE INVENTION

Figure 1:
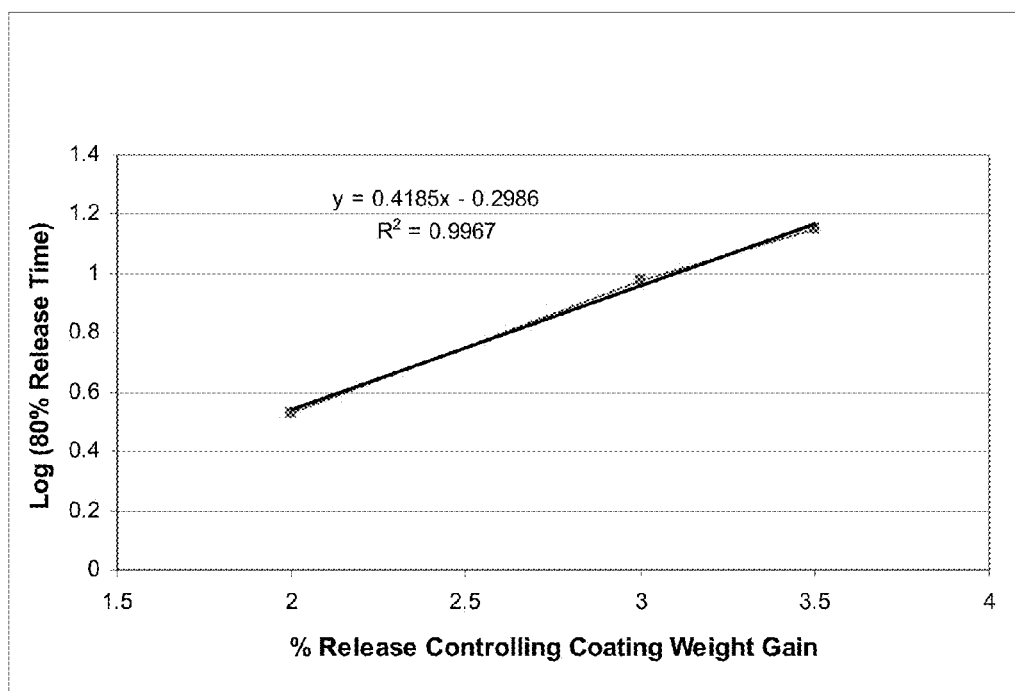
FIG. 1 shows the time of release of 80% of the drug vs. % wt. gain of release controlling coating for cured Surelease® coated extended release beads.

Topiramate is a sulfamate-substituted monosaccharide having the chemical name 2,3:4,5-Di-O-isopropylidene-beta-D-fructopyranose sulfamate. The molecular formula of topiramate is C12H21NO8S, and its chemical structure is represented by formula below:

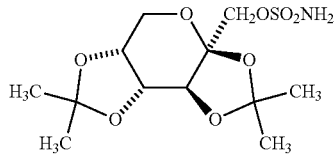

Topiramate is a white crystalline powder that is soluble in alkaline solutions containing sodium hydroxide or sodium phosphate, soluble in acetone, dimethylsulfoxide and ethanol. However, the solubility of topiramate in water at room temperature is only about 9.8 mg/ml. Topiramate is not extensively metabolized and is excreted largely through the urine (Physician's Desk Reference, 60th ed., 2538-2447 (2006)).

Topiramate pharmacokinetics are linear, producing a dose proportional increase in blood plasma concentration levels with increased dosing, and is not significantly affected by food. Patients taking topiramate over prolonged period of time did not develop resistance to the drug. Following oral administration of an immediate release dosage form, topiramate is rapidly absorbed with plasma drug concentrations peaking in approximately 2 hours. The mean elimination half-life is reported to be about 21 hours.

Currently, topiramate is administered in multiple daily doses in part due to the severe side effects exhibited by the immediate release product, especially when taken in a high single dose.

A sustained release topiramate formulation that will be suitable for once-a-day administration and will result in the diminished level or severity of side effects is needed.

The present invention provides sustained release formulation of topiramate wherein the total daily dose of topiramate is provided in an effective once-daily dose while minimizing fluctuations in the blood plasma drug concentration.

The current invention also provides for formulations of topiramate wherein the maximum plasma concentration of topiramate is attenuated as compared to the same amount of topiramate administered as an immediate release formulation BID; therefore some of the side effects of topiramate, such as CNS side effects including but not limited to dizziness, paresthesia, nervousness, psychomotor slowing, confusion, and difficulty with concentration/attention, observed when taking the immediate release product, may be reduced or eliminated.

Formulations of the instant invention are characterized by a maximum steady state plasma concentration (Cmax) of topiramate which is higher than the minimal therapeutically effective concentration, and is in the range of 50% to 125% of the maximum plasma concentration produced by the same amount of topiramate administered as an immediate release formulation BID.

In one embodiment, the novel formulations provide for a relative Cmax in the range of 80% to 125%, as compared to the same amount of topiramate administered as an immediate release formulation BID. In the other embodiment, the invention provides for the Cmax which is lower than the maximum plasma concentration produced by the same amount of topiramate administered as an immediate release formulation BID. The Cmin of the topiramate formulation of the present invention is about equal or higher than a Cmin of an equivalent amount of immediate release topiramate formulation given BID.

Compared to the immediate release topiramate formulation, the sustained release topiramate formulations attenuate the Cmax of topiramate while extending the coverage of plasma concentration above the minimum plasma concentration required therapeutic efficacy. The formulation of the current invention provides for a relative steady state AUC in the range of 80% to 125%, while minimizing the degree of fluctuation, which is preferably in the range of 25% to 90%, as compared to an equivalent amount of immediate release topiramate formulation given in two divided doses (Table 5 and 6).

The present invention additionally provides a sustained release topiramate formulation for the treatment or prevention of a pathological condition in a mammalian subject wherein topiramate is released from the formulation at a sustained rate along a pre-determined release profile. Such release is achieved by incorporation into the formulation of an extended release component (XR) and an optional immediate release component (IR).

The relative amount of each component in the topiramate formulation of the present invention is determined according to the purpose of administration and a pre-determined release profile, and the total amount of topiramate in the formulation varies from 0.5 mg to about 3000 mg. In other words, topiramate or its salt is present in the composition in an amount of from about 0.5% to about 85% by weight, and preferably of from about 2% to about 70% by weight. The term "about" has been recited here and throughout the specification to account for variations, which can arise from inaccuracies in measurement inherent and understood by those of ordinary skill in the chemical and pharmaceutical arts.

The XR component of the formulation of the present invention releases topiramate in a continuous manner and is adjusted in such a way that 80% of the active ingredient is released in vitro in the predetermined period of time. By way of example, and by no means limiting the scope of the invention, the period of time may be not more than 24 hours, not more than 16 hours, not more than 12 hours, not more than 8 hours, or not more than 4 hours, depending on desired attributes of the final product.

In one embodiment, the extended release (XR) component is contained in at least one population of beads coated with a coating that modifies and controls the release of topiramate from the beads (release controlling coating). The release controlling coating is specific for every population of beads and determines the rate of release of topiramate from the given bead population.

The beads useful in the formulation of the present invention comprise an inert carrier, topiramate, a binder, an aforementioned release controlling coating and optionally, an overcoat that provides additional protection from moisture, static charge reduction, taste masking and coloring attributes to the particulates.

The inert carriers useful in the present invention may be selected from, but are not limited to, a group consisting of cellulose spheres, silicon dioxide, starch and sugar spheres. The inert carrier is present in an amount of from about 15% to about 99% by weight, and preferably in an amount of from about 40% to about 97% by weight.

Topiramate is introduced to the inert carrier by techniques known to one skilled in the art, such as drug layering, powder coating, extrusion/spheronization, roller compaction or granulation. Preferably, the introduction method is drug layering by spraying a suspension of topiramate and a binder onto the inert carrier.

The binder may be present in the bead formulation in an amount of from about 0.1% to about 15% by weight, and preferably of from about 0.2% to about 10% by weight. Binders include, but are not limited to starches, microcrystalline cellulose, hydroxypropyl cellulose, hydroxyethyl cellulose, hydroxypropylmethyl cellulose, or polyvinylpyrrolidone.

The release controlling coating specific for every bead population comprises a coating material, and, optionally, a pore former and other excipients. The coating material is preferably selected from a group comprising cellulosic polymers, such as ethylcellulose, methylcellulose, hydroxypropyl cellulose, hydroxypropylmethyl cellulose, cellulose acetate, and cellulose acetate phthalate; polyvinyl alcohol; acrylic polymers such as polyacrylates, polymethacrylates and copolymers thereof, and other water-based or solvent-based coating materials. The release-controlling coating is population-specific in the sense that the rate of release of topiramate from every bead population is controlled by at least one parameter of the release controlling coating, such as the nature of the coating, coating level, type and concentration of a pore former, process parameters and combinations thereof. Thus, changing a parameter, such as a pore former concentration, or the conditions of the curing, as will be discussed in more details below, (see Example 5) allows to change the release of topiramate from any given bead population and to selectively adjust the formulation to the pre-determined release profile. The release profile, in its turn, may be chosen or modified in such a way as to achieve the best treatment modality depending on the specific needs of the patient population and the nature of the condition.

For example, with all things being equal, there exists a mathematical relationship between the release controlling coating level among the cured beads and the 80% in vitro release time. Pre-determined target profiles can therefore be achieved by the interpolation or extrapolation of the relationship curve. For example, when the release controlling coating comprises only ethylcellulose (Surelease®) as a coating material, a logarithmic relationship exists between the % weight gain with the coating and the 80% release time in an in-vitro dissolution test (FIG. 1):

$$\text{Log}(T_{80\% \text{ release}}) = a(\% \text{ coating}) + b.$$

Figure 2:
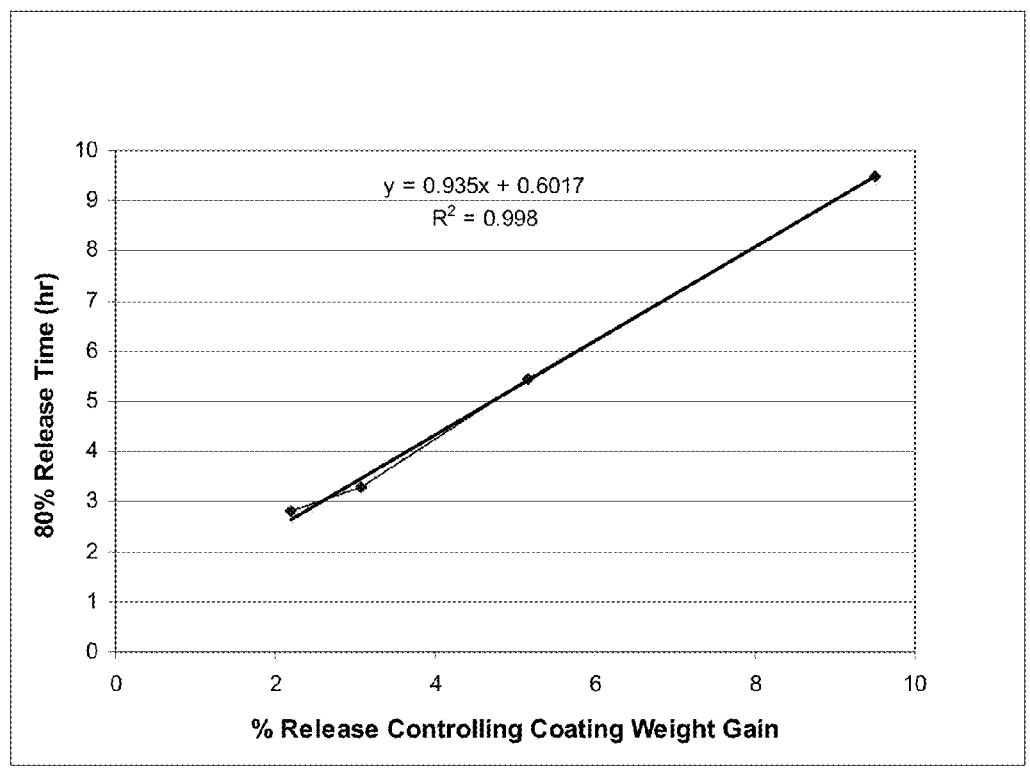
FIG. 2 shows the time of release of 80% of the drug vs. % wt. gain of release controlling coating for cured Surelease®/Opadry® coated extended release beads.

When ethylcellulose/HPMC (Surelease®/Opadry®) mixture is used, for example, 85:15 mixture or 80:20 mixture, a linear relationship exists between the % weight gain with the coating and the 80% release time in an in-vitro dissolution test (FIG. 2):

$$T_{80\% \text{ release}} = a(\% \text{ coating}) + b.$$

Pore formers suitable for use in the release controlling coating herein can be organic or inorganic agents, and include materials that can be dissolved, extracted or leached from the coating in the environment of use. Examples of pore formers include but are not limited to organic compounds such as mono-, oligo-, and polysaccharides including sucrose, glucose, fructose, mannitol, mannose, galactose, sorbitol, pullulan, dextran; polymers soluble in the environment of use such as water-soluble hydrophilic polymers, hydroxyalkylcelluloses, carboxyalkylcelluloses, hydroxypropylmethylcellulose, cellulose ethers, acrylic resins, polyvinylpyrrolidone, cross-linked polyvinylpyrrolidone, polyethylene oxide, Carbowaxes, Carbopol, and the like, diols, polyols, polyhydric alcohols, polyalkylene glycols, polyethylene glycols, polypropylene glycols, or block polymers thereof, polyglycols, poly(α-ω)alkylenediols; inorganic compounds such as alkali metal salts, lithium carbonate, sodium chloride, sodium bromide, potassium chloride, potassium sulfate, potassium phosphate, sodium acetate, sodium citrate, suitable calcium salts, and the like.

The release controlling coating in the current invention can further comprise other additives known in the art such as plasticizers, anti-adherents, glidants, and antifoams.

In some embodiments, it may be further desirable to optionally coat the XR beads with an "overcoat," to provide, e.g., moisture protection, static charge reduction, taste-masking, flavoring, coloring, and/or polish or other cosmetic appeal to the beads. Suitable coating materials for such an overcoat are known in the art, and include, but are not limited to, cellulosic polymers such as hydroxypropylmethylcellulose, hydroxypropylcellulose and microcrystalline cellulose, or combinations thereof (for example various Opadry® coating materials).

Topiramate-containing beads of the present invention may additionally contain enhancers that may be exemplified by, but not limited to, solubility enhancers, dissolution enhancers, absorption enhancers, permeability enhancers, stabilizers, complexing agents, enzyme inhibitors, p-glycoprotein inhibitors, and multidrug resistance protein inhibitors. Alternatively, the formulation can also contain enhancers that are separated from the topiramate beads, for example in a separate population of beads or as a powder. In yet another embodiment, the enhancer(s) may be contained in a separate layer on a topiramate-containing bead either under or above the release controlling coating.

The beads may further comprise other pharmaceutically active agents suitable for use in combination with topiramate for treatment or prevention of a pathological condition. The additional pharmaceutically active agents, without limitation, may be represented by analgesic and anti-inflammatory compounds such as COX-2 inhibitors, nonsteroidal anti-inflammatory drugs (NSAIDs), narcotic drugs such as opiates and morphinomimetics, synthetic drugs with narcotic properties such as tramadol; anticonvulsants such as valproic acid or its derivatives, carbamazepine, oxcarbazepine, gabapentin, and lamotrigine; anorectics or anti-obesity agents such as sibutramine or other, orlistat or other pancreatic lipase inhibitors, diethylpropion, fluoxetine, bupropion, amphetamine, methamphetamine, sertraline, zonisamide, and metformin, as well as medications associated with weight-gain, such as sulfonylurea derivatives, insulin, and thiazolidinediones whose weight-gain effect is tempered by topiramate; anti-hypertensive agents such as diuretics, anti-adrenergics, calcium channel blockers, ACE inhibitors, angiotensin II receptor antagonists, aldosterone antagonists, vasodilators, centrally acting adrenergic drugs, and adrenergic neuron blockers; mood stabilizers such as various forms/salts of lithium, Omega-3 fatty acids and others known in the art, drugs for treatment or prevention of migraines, such as ergot derivatives or triptans, or any other pharmaceutical or nutraceutical ingredient that can be safely and beneficially combined with topiramate.

A relative amount of every bead population in the complete formulation is determined on the basis of the pharmacokinetic data of the separate bead populations and the pre-determined release profile and will be discussed in more detail in Example 6.

In another embodiment, the formulation of the present invention comprises an extended release component as described above, and an immediate release component. The IR component may be an enhanced immediate release composition. The enhanced immediate release composition may be characterized by a faster in vitro topiramate release as compared to the IR formulation. Preferably, at least 80% of an active compound from the enhanced immediate release composition is released in a time period of not more than 30 minutes. More preferably, at least 50% of an active compound from the enhanced immediate release composition is released in a time period of not more than 10 minutes, and at least 25% is dissolved in a time period of not more than 5 minutes after the oral administration. In the most preferred embodiment of the present invention, at least 75% of the active compound is released from the EIR composition in a time period of not more than 10 minutes. The embodiment in which the IR component is an enhanced immediate release composition will be discussed in more details below.

In addition to topiramate and inactive excipients, the EIR composition of the present invention comprises at least one agent selected from a group consisting of complexing agents and enhancing agents.

Without any limitation, the enhancing agents suitable for the present invention may be selected from the solubility enhancing agents, dissolution enhancing agents, absorption enhancing agents, penetration enhancing agents, surface active agents, such as non-ionic surfactants, ionic surfactants or combinations thereof; stabilizers that include antioxidants, preservatives, buffering agents, bases and other known in the art; enzyme inhibitors, p-glycoprotein inhibitors, multidrug resistance protein inhibitors, or any combinations thereof. The representative, but non-limiting examples of these compounds are Vitamin E TPGS, amino acid such as glutamic acid and glycine, sorbitol, mannose, amylose, maltose, mannitol, lactose, sucrose, glucose, xylitose, dextrins such as maltodextrin, Cremophor RH40 (glycerol-polyethylene glycol oxystearate), Gelucire 50/13 (PEG-32 glyceryl palmitostearate), sodium lauryl sulfate, Tween 80 (polyoxyethylene sorbitan monooleate), benzyl alcohol, Span 20 (sorbitan monolaurate), Poloxamer 407, PEG3350, PVP K25, oleic acid, Capmul GMO (glyceryl monooleate), sodium benzoate, cetyl alcohol, sucrose stearate, crospovidone, sodium starch glycolate, crosscarmellose sodium, carboxymethylcellulose, starch, pregelatinized starch, HPMC, substituted hydroxypropylcellulose, microcrystalline cellulose, sodium bicarbonate, calcium citrate, sodium docusate, and menthol, among others. Enhancers can be combined to achieve multiple enhancement effects, for example, solubility enhancement combined with permeability enhancement and p-glycoprotein inhibition, or to provide a synergistic enhancement effect to achieve greater and more efficient enhancement. For example, polyglycolized glycerides (different grades of Gelucire) can be combined with sodium lauryl sulfate to achieve higher solubility enhancement as well as faster dissolution of topiramate.

In one embodiment, the EIR composition comprises a highly soluble complex of topiramate with a complexing agent that is represented by, but not limited to, cyclodextrins, including cyclodextrin derivatives, such as hydroxypropyl-beta-cyclodextrin, beta-cyclodextrin, gamma-cyclodextrin, and alpha-cyclodextrin. The ratio of cyclodextrin to topiramate in the EIR formulation is preferably less than 20:1 and more preferably less than 5:1. In the most preferred embodiment, the complexing agent is hydroxypropyl beta cyclodextrin.

The highly soluble complex of topiramate and cyclodextrin is prepared by mixing topiramate and cyclodextrin together in the presence of water. The concentration of cyclodextrin is preferably high to facilitate the formation of topiramate-enhancer complex. In the case when the complexing agent is hydroxypropyl-beta-cyclodextrin, the concentration of the hydroxypropyl-beta-cyclodextrin solution used for mixing with topiramate is greater than 2%, preferably greater than 20%, and more preferably at least about 40%. The amount of topiramate is determined by a desired ratio of hydroxypropyl-beta-cyclodextrin to topiramate, which is preferably less than 20:1, and more preferably less than 5:1. The mixing time of the complex solution is from about one hour to about 48 hours, and preferably from about 5 hours to about 24 hours. The addition of hydroxypropyl-beta-cyclodextrin and topiramate can be incremental to reduce the viscosity of the complex solution and to achieve better complexation.

In a further embodiment, the EIR component of the present invention is contained in at least one bead population. Topiramate EIR beads can be prepared using processes suitable for bead manufacturing, such as coating of a topiramate suspension, dispersion or solution onto an inert carrier, or by roller compaction, granulation, extrusion/spheronization, or powder coating, and are not limited by the examples cited therein. The enhancing agents of the present invention can be incorporated into the topiramate containing beads, or may be contained in other beads separated from the topiramate containing beads. By way of a non-limiting example, topiramate-containing EIR beads were prepared by coating topiramate dispersion onto an inert carrier such as sugar spheres. The topiramate dispersion, in addition to topiramate in the micronized form or in non-micronized form, can contain one or more enhancers, water and optionally a binder such as hydroxypropylcellullose, hydroxypropylmethylcellulose, polyvinylpyrrolidone and polyvinyl alcohol.

When the formulation is enhanced with complexing agents, the agents may be first mixed with topiramate and a suitable solvent such as water to form the complex. The topiramate-containing complex is then mixed with a binder solution prepared separately to give the coating dispersion. The coating dispersion is then sprayed onto the inert carrier such as sugar spheres using a fluid bed processor.

In an alternative embodiment of the invention, the formulation comprises at least one XR bead population, and at least one additional combination bead population consisting of the extended release beads that have an additional immediate release component layer coated on top of the release controlling coating. This layer may be formed by a suitable loading method such as solution/suspension/dispersion coating, powder coating or wet granulation.

In yet another embodiment, at least part (i.e., more than 0.01%, preferably at least 1%) of the active ingredient may be present in the formulation in a form of micronized particles with the size of from 1 μm to 1000 μm, preferably from 2 μm to about 200 μm, more preferably from 2 μm to about 100 μm. Further, one or more enhancers may be present in the formulations covered by this embodiment. The enhancers are selected from solubility enhancing agents, dissolution enhancing agents, absorption enhancing agents, penetration enhancing agents, surface active agents, such as non-ionic surfactants, ionic surfactants or combinations thereof; stabilizers that include antioxidants, preservatives, buffering agents, bases and other known in the art; enzyme inhibitors, p-glycoprotein inhibitors, multidrug resistance protein inhibitors, or any combinations thereof. Preferably, the enhancer is a solubility enhancer or a dissolution enhancer.

The topiramate formulation of the present invention may be formulated in a dosage form selected from a tablet, a pill, a capsule, a caplet, a troche, a sachet, a cachet, a pouch, sprinkles, or any other form suitable for oral administration.

Figure 5:
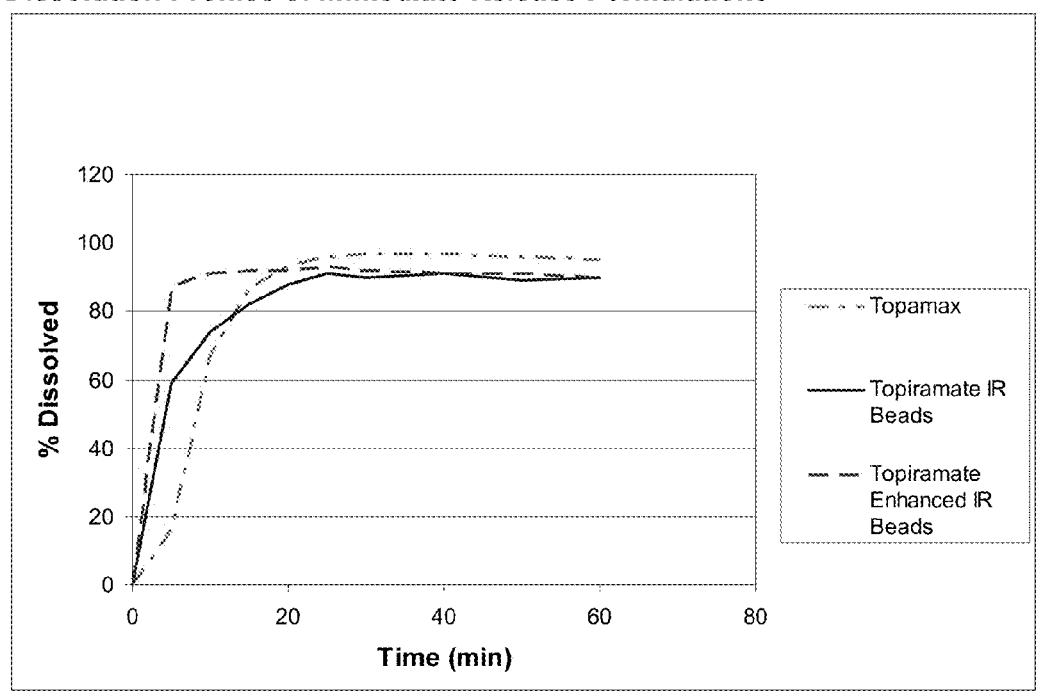
FIG. 5 shows the dissolution profiles of Topamax®, topiramate IR beads, and topiramate enhanced immediate release beads.

In one embodiment of the invention, the dosage form is a gelatin capsule containing the XR component in a form of at least one population of beads, and an optional IR component. The IR component, when present, may be in a form of a powder, or may also be contained in at least one population of beads to achieve faster dissolution of topiramate (FIG. 5).

In an alternative embodiment, part of the total amount of the active ingredient may be incorporated into the aforementioned bead populations that will be contained inside an enclosure such as a capsule, and the rest of the active ingredient can be loaded on the outside of the enclosure by a suitable loading method such as solution/suspension/dispersion coating or powder coating or wet granulation. For example, a part of the immediate release topiramate formulation can be loaded by coating on the outside of a capsule that contains within it other populations of topiramate such as extended release topiramate. This dosage form can provide almost instantaneous dissolution of the initial portion of topiramate dose from the outside of the capsule, followed by a sustained release of the rest of topiramate from inside the capsule.

In a further embodiment of the invention, the dosage form is a tablet. Without imposing any limitations, this embodiment may be exemplified by a multilayered tablet that comprises at least one layer containing the extended release component, and at least one layer comprising the immediate release component, wherein the IR component may or may be not an EIR composition.

The last two embodiments are especially beneficial when fast onset of action followed by sustained release is preferred, as is for example in the cases of a breakthrough migraine episode.

The current invention additionally encompasses a method of preparing formulations of topiramate, comprising an extended release component, and an optional immediate release component, wherein topiramate is released from the formulation at the sustained rate along the pre-determined release profile. The method comprises the following steps:

1. determining the desired release profile;
2. determining specific amounts of the extended release component and the immediate release component necessary to produce the pre-determined release profile; and
3. incorporating the specified amounts of the components into the formulation.

In one embodiment, the method comprises a step for providing an immediate release component, which may be an enhanced immediate release composition.

In another embodiment, the method includes a process for providing an extended release component contained in at least one population of beads characterized by its own rate of release, wherein the process includes the steps of:

1. forming at least one population of topiramate-containing beads;
2. coating each population of beads with its own coating solution;
3. curing the coating for a period of time to produce a release controlling coating specific for each bead population, and
4. incorporating the beads into the formulation.

The exact amount of beads of every population incorporated into the formulation and into the final dosage form is determined using the linear superposition principle (WinNonLin) on the basis of the pharmacokinetic data of the separate bead populations and the pre-determined release profile (Example 6).

Release profiles of XR topiramate beads can be selectively adjusted, modified or stabilized by curing the beads at an elevated temperature. This process is well known in the art. However, it was unexpectedly discovered that curing the beads in the curing apparatus in the presence of at least one suitable solvent dramatically reduces the curing time necessary to produce a desired release profile and a level of stability. The curing process that previously required up to two weeks can be carried out by the method of current invention in several hours.

The assisting solvents can be selected from those solvents that can dissolve or partially dissolve the coating material, or those that can induce or assist the coalescence or molecular relaxation of the coating material, or those that can reduce electrostatic charge on the dosage forms during curing and those that can facilitate curing at a higher temperature. Examples of these solvents include but are not limited to organic solvents, such as alcohols, ketones, ethers, esters, amides, amines, hydrocarbons including substituted hydrocarbons such as chlorinated hydrocarbons and aromatic hydrocarbons, furans, sulfoxides, organic acids, phenols, super-critical fluids; ammonia; and water, buffered water, or water solutions of other inorganic or organic compounds, and their combinations. Preferably, water, water-alcohol mixture, water-ketone mixture, water-ammonia mixture, or water-organic acid (for example water-acetic acid) mixture, or combinations thereof are used as the assisting solvents.

The curing of the dosage form normally is done in an apparatus that can operate at elevated temperatures and that can deliver the assisting solvents by means such as spray, injection, or vaporization. In the embodiment of the invention when the assisting solvent is sprayed or injected into the curing apparatus, the stream of solvent is introduced directly onto the coated beads. The amount of the solvent necessary to produce the desired effect, such as the desired release parameters and stabilization of the coating, depends on the nature of the solvent and the method of solvent delivery.

Typically, when the vaporization method is used, the organic solvents and aqueous solutions may be used in the wide range of vapor concentrations varying from 2% to more than 100%, providing an unsaturated, saturated or an oversaturated atmosphere. The pure water, however, has to be used in such an amount as to provide at least a saturated or, preferably, an oversaturated atmosphere in the curing apparatus. At least during the delivery of assisting solvents, the coated beads are mixed or agitated either continuously or in a pulsed manner.

In an alternative embodiment of the invention, hot water steam is introduced into the curing apparatus for a pre-selected period of time. The steam serves simultaneously as a solvent and as a source of heat for the beads. Introduction of steam is followed by a drying period.

This method of curing the release controlling coating results in many benefits including the dramatically shortened curing time, increased stability and modification of the release profile, and is not limited to topiramate containing beads, but includes the curing of any microparticles regardless of the drug.

Specifically, active ingredient containing beads, with or without the optional over-coat, are charged to a fluid bed processor or a pan coater and heated to a desired curing temperature range, for example 40° C. to 80° C. for sustained release dosage forms containing ethylcellulose (Surelease®), and 40° C. to 70° C. for sustained release dosage forms containing acrylic polymers (Eudragit® RS and Eudragit® RL). The assisting solvent or solvents, such as water or alcohol-water mixture, are sprayed onto the beads while mixing by, for example, fluidizing or rotating. Alternatively, the process is carried out in an oven where hot steam is introduced as previously discussed. Solvent-assisted curing is carried out to a desired curing time length, either in one curing period or in multiple, separate curing periods. The dosage forms can be further dried for a short period of time to remove residual solvents.

The solvent-assisted curing process significantly accelerates the curing of release controlling coating on active ingredient containing beads as compared to the heat-only curing of the same. In most instances, less than 4 hours of solvent-assisted curing resulted in more complete curing of the extended release dosage forms than 2 weeks of heat-only oven curing of the same dosage forms.

The present invention also presents a method of treatment or prevention of a pathological condition in a mammalian subject, comprising orally administering to the subject a therapeutically effective amount of a novel topiramate formulation of the instant invention, wherein topiramate is released from the formulation at a sustained rate along the pre-determined release profile. The method of the current invention possesses the flexibility to selectively adjust the pharmacokinetics of the administered formulations depending on the nature of the condition and needs of the patients due to the novel design of the topiramate formulation that comprises an extended release component and an optional immediate release component, and the release profiles of both components can be selectively modified during the preparation process as described above to comply with the predetermined release profile.

The pathological condition that may be treated by a method of the present invention is a neurological condition, psychiatric condition, diabetes and related disorders, cardiovascular condition, obesity, and any other condition or disorder that may be treated or prevented by the topiramate administration.

The neurological disorders that may be treated or prevented by a formulation of the present invention include, but are not limited to, epilepsy, migraine, essential tremor, restless limb syndrome, cluster headaches, neuralgia, neuropathic pain, Tourrette's syndrome, infantile spasms, perinatal hypoxia ischemia and related damage, chronic neurodegenerative disorders, acute neurodegeneration, and ALS.

Psychiatric disorders that may be treated or prevented by a formulation of the present invention include, but are not limited to bipolar disorder, dementia, depression, psychosis, mania, anxiety, schizophrenia, obsessive-compulsive disorder, post-traumatic stress disorder, ADHD, impulse control disorders, border line personality disorder, addiction, and autism.

Formulations of the present invention may be also used for the treatment and prevention of diabetes and related disorders, such as type II diabetes mellitus, diabetic retinopathy, impaired oral glucose tolerance, diabetic skin lesions, diabetic neuropathy, Syndrome X and elevated blood glucose levels; ocular disorders, including but not limited to glaucoma and macular degeneration; cardiovascular disorders represented but not limited to elevated blood pressure and elevated lipids; obesity; asthma; autoimmune disorders; sleep apnea and sleep disorders. The formulations may be also used for inducing weight loss or promoting wound healing, or for any other condition, not specified above, wherein the use of topiramate is indicated.

The invention will be further illustrated by the following Examples, however, without restricting its scope to these embodiments.

EXAMPLES

Example 1

Extended Release Beads Preparation Topiramate Drug Layering on Sugar Spheres—The "Core"

An aqueous suspension of 10-20% (w/w) topiramate (particle size 90% vol. NMT 30 micrometer, 50% vol. NMT 15 micrometer and 10% vol. NMT 5 micrometer) and 0.5-4% (w/w) HPMC or other aqueous binder can be used as the drug layering coating solution. A fluid bed suited for Wurster-spray is assembled and charged with inert carriers such as sugar spheres. The coating suspension is sprayed onto the bed to evenly coat the inert carriers to a desired topiramate loading level. Higher binder concentration in the coating solution may be used for smaller size inert carrier and higher topiramate loading. Inlet airflow rate and product temperature are adjusted to keep the batch from spray-drying the coating material or over-wetting the spheres.

Coating of the Core with a Release Controlling Coating

A dispersion of a cellulosic polymer such as ethylcellulose and methylcellulose can be used to coat the core in the current invention. Ethylcellulose dispersion (Surelease®) can be diluted to a final concentration of about 10% to about 20% and with or without the use of other ingredients such as pore formers. A fluid bed suited for Wurster-spray is assembled and charged with the cores prepared in Example 1. The release controlling coating dispersion is sprayed onto the bed to evenly coat the core to a desired coating level as exemplified in Table 1.

TABLE 1

| Composition and process Parameters for the extended Release | | | | | | | |
|---|---|---|---|---|---|---|---|
| | XR1a | XR1b | XR1c | XR2a | XR2b | XR2c | XR2d |
| RC* coating material | Ethyl-cellulose (Surelease) | Ethyl-cellulose (Surelease) | Ethyl-cellulose (Surelease) | Ethyl-cellulose (Surelease) | Ethyl-cellulose (Surelease) | Ethyl-cellulose (Surelease) | Ethyl-cellulose (Surelease) |
| Pore-former | — | — | Opadry ® Clear | — | — | Opadry ® Clear | Opadry ® Clear |
| RC coating material to pore-former ratio | — | — | 80:20 | — | — | 80:20 | 80:20 |
| RC coating level | 2% | 4% | 3% | 3% | 3% | 6.5% | 6.5% |
| Product temperature during coating | 20° C.-60° C. | 20° C.-60° C. | 20° C.-60° C. | 20° C.-60° C. | 20° C.-60° C. | 20° C.-60° C. | 20° C.-60° C. |

TABLE 1-continued

| | | | | | | | |
|---|---|---|---|---|---|---|---|
| Over-coat material | — | Opadry ® AMB White | Opadry ® AMB White | — | Opadry ® AMB White | — | Opadry ® AMB White |
| Over-coat coating level | — | 1.5% | 1.5% | — | 1.5% | — | 1.5% |
| Curing method | Fluid bed/ water, or oven | Fluid bed/ water, or oven | Fluid bed/ water, or oven | Fluid bed/ water, or oven | Fluid bed/ water, or oven | Fluid bed/ water, or oven | Fluid bed/ water, or oven |

| Topiramate Beads | | | | | | |
|---|---|---|---|---|---|---|
| | XR3 | XR4 | XR5 | XR6 | XR7 | XR8 |
| RC coating material | Ethylcellulose (Surelease) | Ethylcellulose (Surelease) | Ethylcellulose (Surelease) | Ethylcellulose (Surelease) | Ethylcellulose (Surelease) | Acrylic polymers (Eudragit ® RL30D/ RS30D) |
| Pore-former | — | Cellulosic polymers (Opadry ® Clear) | Cellulosic polymers (Opadry ® Clear) | Cellulosic polymers (Opadry ® Clear) | Cellulosic polymers (Opadry ® Clear) | — |
| RC coating material to pore-former ratio | — | 80:20 | 80:20 | 80:20 | 85:15 | — |
| RC coating level | 3.7% | 3.1% | 5.2% | 9.5% | 15% | 15% |
| Product temperature during coating | 20° C.- 60° C. | 20° C.- 60° C. | 20° C.- 60° C. | 20° C.- 60° C. | 20° C.- 60° C. | 20° C.- 60° C. |
| Over-coat material | — | — | — | — | — | — |
| Over-coat coating level | — | — | — | — | — | — |
| Curing method | Fluid bed/ water, or oven | Fluid bed/ water, or oven | Fluid bed/ water, or oven | Fluid bed/ water, or oven | Fluid bed/ water, fluid bed/5% alcohol- water, or oven | Fluid bed/ water, fluid bed/5% alcohol- water, or oven |

*RC - Release Controlling

Example 2

Method of Topiramate-Hydroxypropyl-beta-cyclodextrin Complex Bead Preparation

Approximately half of the intended amount of topiramate was added to the water with constant mixing followed by sprinkling of hydroxypropyl-beta-cyclodextrin into the dispersion. Once the dispersion became significantly less viscous, more drug substance was added followed by sprinkling of more hydroxypropyl-beta-cyclodextrin. The drug and hydroxypropyl-beta-cyclodextrin addition steps were repeated, and the dispersion was mixed for 12-18 hours. Separately, hydroxypropylmethylcellulose was dissolved in water. The above topiramate-hydroxypropyl-beta-cyclodextrin dispersion and hydroxypropylmethylcellulose solution were mixed together for 15 to 30 minutes and the mixture was screened through an 80-mesh sieve. The resultant dispersion was sprayed onto sugar spheres using a fluid bed processor to yield the enhanced immediate release beads (Table 2).

TABLE 2

Hydroxypropyl-beta-cyclodextrin - Topiramate EIR Bead Compositions

| | Percentage (w/w) in Beads | | | |
|---|---|---|---|---|
| Component | EIR-1 (HPBCD: Drug = 3:2)* | EIR-2 (HPBCD: Drug = 3:2)* | EIR-3 (HPBCD: Drug = 1:1)* | EIR-4 (HPBCD: Drug = 1:2)* |
| Topiramate | 25.0 | 3.3 | 28.9 | 33.3 |
| Hydroxypropyl- beta-cyclodextrin | 37.5 | 4.95 | 28.9 | 16.7 |
| Hydroxypropyl- methylcellulose | 3.1 | 0.41 | 2.4 | 4.2 |
| Sugar spheres | 34.4 | 91.34 | 39.8 | 45.8 |

*HPBCD:Drug - Hydroxypropyl-beta-cyclodextrin to drug substance ratio

Example 3

Topiramate EIR Beads Containing Non-Complexing Enhancers

Topiramate is dispersed in a binder solution, such as hydroxypropylmethylcellulose solution, that contains an appropriate amount of enhancer or enhancers such as d-alpha-tocopheryl polyethylene glycol 1000 succinate (vitamin E TPGS) and sodium lauryl sulfate combination, polyoxyl hydrogenated castor oil (different grades of Cremophor RH), polyglycolized glycerides (different grades of Gelucire), polyglycolized glycerides (different grades of Gelucire) combined with sodium lauryl sulfate, or combinations thereof. The resultant dispersion is sprayed onto an inert carrier such as sugar spheres using a fluid bed processor to achieve a desired drug load (Table 3).

TABLE 3

Enhanced Immediate Release Topiramate Bead Compositions

| Component | Percentage (w/w) in Beads | | |
|---|---|---|---|
| | EIR-5 | EIR-6 | EIR-7 |
| Topiramate | 36.8 | 37.9 | 36.4 |
| Sodium lauryl sulfate | 0.7 | 0.5 | — |
| D-alpha-tocopheryl polyethylene glycol 1000 succinate | 7.3 | — | — |
| Polyoxyl hydrogenated castor oil (Cremophor RH40) | — | — | 9.1 |
| Polyglycolized glycerides (Gelucire 50/13) | — | 4.7 | — |
| Hydroxypropylmethylcellulose | 4.6 | 4.8 | 4.5 |
| Sugar spheres | 50.6 | 52.1 | 50.0 |

Example 4

Topiramate EIR Beads Containing Micronized Particles

Miconized or non-micronized topiramate is dispersed in a solution with or without heating, optionally containing dissolution enhancing agents such as mannose, maltose, mannitol, lactose, maltodextrin and sodium starch glucolate, and optionally containing one or more additional enhancers such as PEG3350, sodium lauryl sulfate, sodium docusate, polyoxyethylene sorbitan monooleate and Poloxamers, under such process parameters that topiramate particles that remain undissolved have a particle size of about 2 micron to about 30 micron. A particle size reduction device such as a homogenizer can also be used to reduce the particle size of undissolved topiramate. The resultant topiramate dispersion is then sprayed onto inert carriers such as sugar spheres in a coating processor such as a fluid bed processor. The formulations obtained are represented in the Table 4:

TABLE 4

Topiramate EIR Beads containing micronized particles

| | Percentage (w/w) in Beads | | | | | |
|---|---|---|---|---|---|---|
| | EIR-8 | EIR-9 | EIR-10 | EIR-11 | EIR-12 | EIR-13 |
| Topiramate | 3.2 | 26.0 | 25.0 | 3.2 | 26.0 | 26.0 |
| Mannose | 0.4 | 5.0 | 3.3 | 2.0 | 10.0 | 10.0 |
| Maltrin 250 | — | — | 1.0 | 1.0 | — | — |
| PEG3350 | 1.0 | 15.0 | — | — | — | 10.0 |
| Sodium lauryl sulfate | — | — | — | — | 0.5 | — |
| Hydroxypropyl-beta-cyclodextrin | — | 37.5 | — | — | — | — |
| D-alpha-tocopheryl polyethylene glycol 1000 succinate | — | — | — | — | 2.0 | — |
| Polyoxyl hydrogenated castor oil (Cremophor RH40) | — | — | — | — | — | 2.0 |
| Sugar spheres | 95.4 | 54.0 | 33.2 | 93.8 | 61.5 | 52.0 |

Example 5

Method of Curing Beads

The topiramate beads coated with a release controlling coating, with or without an overcoat, can be cured using the above-mentioned solvent-assisted curing process, or using the heat-only curing process, to a desired curing level and preferably to complete curing.

Specifically, the core is coated to a desired coating level with a solution or dispersion of the release controlling coating material, with or without the above-mentioned additives such as pore-formers, using a fluid bed processor or any other suitable apparatus for coating of the core. Product temperature is controlled at a desirable range, for example 20° C. to 60° C. for the coating of ethylcellulose (Surelease®) and 20° C. to 60° C. for acrylic polymers (Eudragit® RL and Eudragit® RS grades). An optional overcoat with materials such as cellulosic polymers (various Opadry®) is applied thereafter. Curing of the sustained release topiramate beads is carried out either in an oven at 40° C. to 80° C. for Surelease® containing beads or at 40° C. to 70° C. for Eudragit® RL or RS containing beads, or in a fluid bed processor with or without the use of assisting solvents at similar product temperatures.

For curing that uses assisting solvents, the assisting solvent can be delivered through top spray, bottom spray, side spray or injection, or introduced by vaporization. Preferably, water, water-alcohol mixture, water-ketone mixture, water-ammonia mixture, or water-organic acid (for example water-acetic acid) mixture, or combinations thereof are used as the assisting solvents.

Example 6

Figure 3:
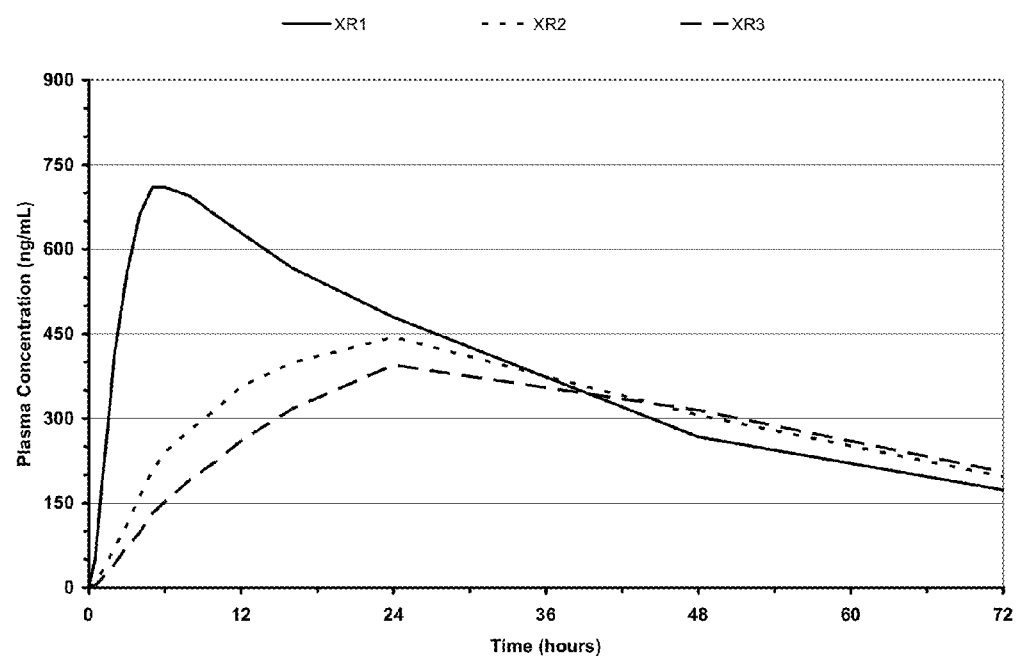
FIG. 3 shows mean (n=16) pharmacokinetic profiles for bead populations XR1, XR2 and XR3.
Figure 4:
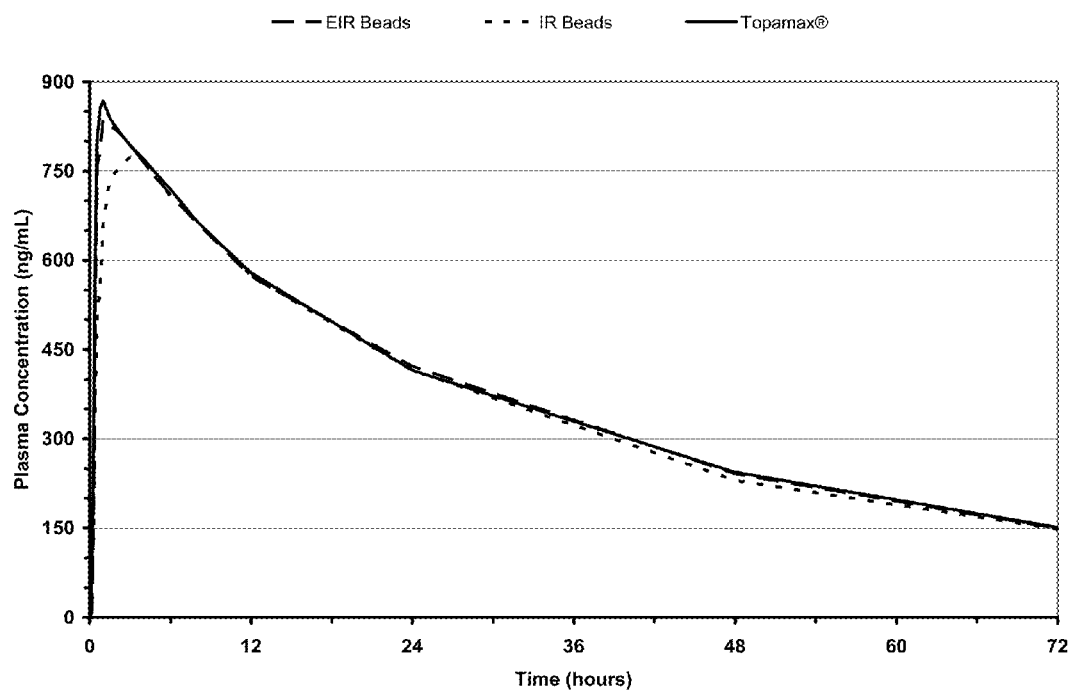
FIG. 4 shows mean (n=16) pharmacokinetic profiles for the immediate release formulations.

Sustained Release Formulations of Topiramate a. Plasma concentration versus time curves for the topiramate formulations containing extended release and immediate release bead populations are simulated using WinNonlin Version 5.0.1 based on the pharmacokinetic data on the separate bead populations that were generated in a comparative randomized single-dose 6-way crossover study in healthy adult volunteers. The study included administration of a 50 mg oral dose of three extended release compositions, designated here as XR1, XR2 and XR3, two immediate release compositions ((Topamax®, Ortho-McNeil Neurologics, Inc.) (25 mg BID), and an immediate release bead formulation) and an enhanced immediate release (IR) bead composition. The single dose topiramate plasma concentration profiles for XR1, XR2 and XR3 are shown in FIG. 3. The single dose topiramate plasma concentration profiles for IR are shown in FIG. 4. The data are projected to a steady-state (SS) with a 24 h dosing interval for the sustained release compositions and a 12 h dosing interval for Topamax, using the linear superposition principle (WinNonlin). The extended release populations XR1, XR2 and XR3, and an immediate release (IR) population are selected in such a way as to be defined by at least one of the three following sets of conditions:

1. for the steady state,
   for XR1, $1.70 C_{maxIR} >= C_{maxXR1} >= 1.30 C_{maxIR}$
   for XR2, $0.40 C_{maxIR} >= C_{maxXR2} >= 0.20 C_{maxIR}$
   for XR3, $0.25 C_{maxIR} >= C_{maxXR3} >= 0.05 C_{maxIR}$ 2. for in-vitro dissolution,
   for XR1, $1.5\ h <= T_{80\%} <= 4\ h$
   for XR2, $5\ h <= T_{80\%}\% <= 8\ h$
   for XR3, $8\ h < T_{80\%} <= 10\ h$ 3. for a single initial dose in-vivo,
   for XR1, $4\ h <= T_{max} <= 8.5\ h$
   for XR2, $T_{max} >= 16\ h$
   for XR3, $T_{max} >= 16\ h$.

Optionally, the immediate release bead population is composed of enhanced immediate release (EIR) beads such that at least one condition is true: a. for the steady state, $2.40\ CmaxIR >= CmaxEIR >= 1.20\ CmaxIR$; b. for in-vitro dissolution, $T80\% <= 30$ min; c. for a single initial dose in-vivo, $Tmax <= 2\ h$.

The results of the pharmacokinetic simulation for the seven exemplary formulations are summarized in Table 5 below. These formulations are selected as examples only, and in no way limit the range, compositions or properties of the formulations covered by the present invention.

TABLE 5

Composition and Pharmacokinetic data of Multi-bead Formulations

|  | #1 | #2 | #3 | #4 | #5 | #6 | #7 |
|---|---|---|---|---|---|---|---|
| % XR1 | 20 | 50 | 0 | 10 | 10 | 15 | 0 |
| % XR2 | 80 | 0 | 85 | 85 | 80 | 70 | 100 |
| % XR3 | 0 | 50 | 0 | 0 | 0 | 15 | 0 |
| % IR | 0 | 0 | 15 | 5 | 10 | 0 | 0 |
| Rel. BA (%), SS | 98.5 | 100.5 | 96.6 | 97.4 | 97.6 | 97.3 | 96.0 |
| Degree of fluctuation, SS | 0.15 | 0.22 | 0.14 | 0.14 | 0.15 | 0.13 | 0.09 | b. based on the results of WinNonlin simulation discussed in part (a), formulations #1 (A), #3 (B), and #4 (C) were tested in the comparative randomized multi-dose 4-way study following a once a day 50 mg oral dose of three controlled release formulations and a 25 mg twice a day oral doses of Topamax® in healthy adult volunteers.

The results of the study are summarized in Table 6 and FIG. 6:

TABLE 6

Pharmacokinetic study data for Multi-bead Formulations

|  | #1 A | #3 B | #4 C | Control (Topamax) |
|---|---|---|---|---|
| % XR1 | 20 | 0 | 10 | — |
| % XR2 | 80 | 86 | 84 | — |
| % XR3 | 0 | 0 | 0 | — |
| % IR | 0 | 14 | 6 | — |

TABLE 6-continued

Pharmacokinetic study data for Multi-bead Formulations

|  | #1 A | #3 B | #4 C | Control (Topamax) |
|---|---|---|---|---|
| Rel. BA (%), SS | 92 | 93 | 95 | 100 |
| Relative Degree of fluctuation, SS | 73% | 72% | 66% | 100% |

What is claimed is:

1. A sustained release formulation of topiramate comprising topiramate as an active ingredient, which is released from the formulation along a pre-determined release profile, the formulation comprising:
   (a) an extended release (XR) topiramate-containing component, comprising a coating material selected from the group consisting of cellulosic polymers and acrylic polymers, and, optionally,
   (b) an immediate release (IR) topiramate-containing component comprising:
      (i) a complexing agent selected from the group consisting of hydroxypropyl-beta-cyclodextrin, beta-cyclodextrin, gamma-cyclodextrin, alpha-cyclodextrin, cyclodextrin, and cyclodextrin derivative, and/or
      (ii) an enhancing agent selected from the group consisting of Vitamin E TPGS, glutamic acid, glycine, sorbitol, mannose, amylose, maltose, mannitol, lactose, sucrose, glucose, xylitose, dextrins, glycerol-polyethylene glycol oxystearate, polyethylene glycol-32 glyceryl palmitostearate, sodium lauryl sulfate, polyoxyethylene sorbitan monooleate, benzyl alcohol, sorbitan monolaurate, polyethylene-polypropylene glycol, polyethylene glycol-3350, polyvinylpyrrolidone-K25, oleic acid, glyceryl monooleate, sodium benzoate, cetyl alcohol, sucrose stearate, crospovidone, sodium starch glycolate, croscarmellose sodium, carboxymethylcellulose, starch, pregelatinized starch, hydroxypropylmethylcellulose (HPMC), substituted hydroxypropylcellulose, microcrystalline cellulose sodium bicarbonate, calcium citrate, sodium docusate, menthol, and combinations thereof,
   wherein the XR component releases topiramate in a continuous manner and such that greater than or equal to about 80% of the topiramate is released in vitro in less than or equal to about 4 hours.

2. The formulation of claim 1, wherein the XR component is contained in at least one population of beads.

3. The formulation of claim 1, comprising an IR component such that 80% of the topiramate is released in not more than 1 hour.

4. The formulation according to claim 1, wherein the XR component further comprises a binder selected from the group consisting of starches, microcrystalline cellulose, hydroxypropyl cellulose, hydroxyethyl cellulose, hydroxypropylmethyl cellulose, and polyvinylpyrrolidone.

5. The formulation according to claim 1, wherein the XR component further comprises a pore former selected from the group consisting of glucose, fructose, mannitol, mannose, galactose, sorbitol, pullulan, dextran, hydroxyalkylcelluloses, carboxyalkylcelluloses, hydroxypropylmethylcellulose, cellulose ethers, acrylic resins, polyvinylpyrrolidone, crosslinked polyvinylpyrrolidone, polyethylene oxide, carbomer, diols, polyols, polyhydric alcohols, polyalkylene glycols, polyethylene glycols, polypropylene glycols or block polymers thereof, polyglycols, poly(α-ω)alkylenediols; alkali metal salts and alkaline earth metal salts, and combinations thereof.

6. The formulation of claim 1, wherein at least a part of the active ingredient is in a form of micronized particles.

7. The formulation of claim 1, wherein the formulation is in a dosage form of a capsule or sprinkles.

8. The formulation of claim 1, wherein the total amount of topiramate in the formulation is from 0.5 to 3000 mg.

9. The formulation of claim 1, wherein the XR component comprises an inert carrier selected from the group consisting of cellulose spheres, silicon dioxide, starch and sugar spheres.

10. The formulation of claim 1, wherein the release controlling coating comprises ethylcellulose, methylcellulose, hydroxypropyl cellulose, hydroxypropylmethyl cellulose, cellulose acetate, cellulose acetate phthalate, polyvinyl alcohol, polyacrylates, polymethacrylates or copolymers thereof.

11. The formulation of claim 1, wherein the formulation provides for a maximum steady state plasma concentration (Cmax) of topiramate which is in the range from 50% to 125% of the maximum plasma concentration produced by the same amount of topiramate administered as an immediate release formulation BID.

12. The formulation of claim 1, wherein the formulation provides for a relative steady state AUC in the range of 80% to 125% of the AUC of the same amount of topiramate administered as an immediate release formulation BID.

13. The formulation of claim 1, further comprising an additional pharmaceutically active ingredient in combination with topiramate.

14. A sustained release formulation of topiramate comprising topiramate as an active ingredient, which is released from the formulation along a pre-determined release profile, the formulation comprising:
　(a) an extended release (XR) topiramate-containing component, comprising a coating material selected from the group consisting of cellulosic polymers and acrylic polymers, and, optionally,
　(b) an immediate release (IR) topiramate-containing component comprising:
　　(i) a complexing agent selected from the group consisting of hydroxypropyl-beta-cyclodextrin, beta-cyclodextrin, gamma-cyclodextrin, alpha-cyclodextrin, cyclodextrin, and cyclodextrin derivative, and/or
　　(ii) an enhancing agent selected from the group consisting of Vitamin E TPGS, glutamic acid, glycine, sorbitol, mannose, amylose, maltose, mannitol, lactose, sucrose, glucose, xylitose, dextrins, glycerol-polyethylene glycol oxystearate, polyethylene glycol-32 glyceryl palmitostearate, sodium lauryl sulfate, polyoxyethylene sorbitan monooleate, benzyl alcohol, sorbitan monolaurate, polyethylene-polypropylene glycol, polyethylene glycol-3350, polyvinylpyrrolidone-K25, oleic acid, glyceryl monooleate, sodium benzoate, cetyl alcohol, sucrose stearate, crospovidone, sodium starch glycolate, croscarmellose sodium, carboxymethylcellulose, starch, pregelatinized starch, hydroxypropylmethylcellulose (HPMC), substituted hydroxypropylcellulose, microcrystalline cellulose sodium bicarbonate, calcium citrate, sodium docusate, menthol, and combinations thereof,
　wherein the XR component releases topiramate in a continuous manner and such that greater than or equal to about 80% of the topiramate is released in vitro in less than or equal to about 12 hours.

15. A method of treatment of a neurological and/or psychiatric condition selected from the group consisting of epilepsy, migraine, essential tremor, restless limb syndrome, cluster headaches, neuralgia, neuropathic pain, Tourrette's syndrome, infantile spasms, bipolar disorder, dementia, depression, psychosis, mania, anxiety, schizophrenia, obsessive-compulsive disorder, post-traumatic stress disorder, attention deficit hyperactivity disorder (ADHD), impulse control disorders, border line personality disorder, addiction, autism, chronic neurodegenerative disorders, acute neurodegeneration, and amyotropic lateral sclerosis (ALS), comprising orally administering to a mammalian subject a therapeutically effective amount of a sustained release formulation according to claim 1.

16. The method of claim 15, wherein the condition is epilepsy.

17. The method of claim 15, wherein the condition is migraine.

18. A method of treatment of a neurological and/or psychiatric condition selected from the group consisting of epilepsy, migraine, essential tremor, restless limb syndrome, cluster headaches, neuralgia, neuropathic pain, Tourrette's syndrome, infantile spasms, bipolar disorder, dementia, depression, psychosis, mania, anxiety, schizophrenia, obsessive-compulsive disorder, post-traumatic stress disorder, attention deficit hyperactivity disorder (ADHD), impulse control disorders, border line personality disorder, addiction, autism, chronic neurodegenerative disorders, acute neurodegeneration, and amyotropic lateral sclerosis (ALS), comprising orally administering to a mammalian subject a therapeutically effective amount of a sustained release formulation according to claim 14.

19. The method of claim 18, wherein the condition is epilepsy.

20. The method of claim 18, wherein the condition is migraine.

\* \* \* \* \*

UNITED STATES PATENT AND TRADEMARK OFFICE
CERTIFICATE OF CORRECTION

| | | |
|---|---|---|
| PATENT NO. | : 8,877,248 B1 | Page 1 of 1 |
| APPLICATION NO. | : 14/330423 | |
| DATED | : November 4, 2014 | |
| INVENTOR(S) | : Liang et al. | |

It is certified that error appears in the above-identified patent and that said Letters Patent is hereby corrected as shown below:

In the claims

Claim 1, column 20, line 44: "…microcrystalline cellulose sodium bicarbonate,…" should read -- …microcrystalline cellulose, sodium bicarbonate,… --

Claim 10, column 21, line 15: "…wherein the release controlling coating comprises…" should read -- …wherein the coating material comprises… --

Claim 14, column 22, line 9: "…microcrystalline cellulose sodium bicarbonate,…" should read -- …microcrystalline cellulose, sodium bicarbonate,… --

Claim 15, column 22, line 26: "…amyotropic…" should read -- …amyotrophic… --

Claim 18, column 22, line 45: "…amyotropic…" should read -- …amyotrophic… --

Signed and Sealed this
First Day of March, 2016

Michelle K. Lee
*Director of the United States Patent and Trademark Office*